(12) United States Patent
Chen

(10) Patent No.: US 9,186,660 B2
(45) Date of Patent: Nov. 17, 2015

(54) SOLID ACID CATALYST AND METHOD FOR PREPARING AND USING THE SAME

(71) Applicant: Jiangsu Sinorgchem Technology Co., Ltd., Taizhou, Jiangsu Province (CN)

(72) Inventor: Xinmin Chen, Shanghai (CN)

(73) Assignee: Jiangsu Sinorgchem Technology Co., Ltd., Taizhou, Jiangsu Province (CN)

( * ) Notice: Subject to any disclaimer, the term of this patent is extended or adjusted under 35 U.S.C. 154(b) by 348 days.

(21) Appl. No.: 13/623,037

(22) Filed: Sep. 19, 2012

(65) Prior Publication Data

US 2013/0015407 A1    Jan. 17, 2013

Related U.S. Application Data

(62) Division of application No. 12/943,930, filed on Nov. 10, 2010, now Pat. No. 8,293,137.

(30) Foreign Application Priority Data

Dec. 30, 2009  (CN) .......................... 2009 1 0215840
Feb. 12, 2010  (CN) .......................... 2010 1 0110589

(51) Int. Cl.

| | |
|---|---|
| C09K 15/08 | (2006.01) |
| B01J 31/10 | (2006.01) |
| B01J 31/02 | (2006.01) |
| C07D 215/06 | (2006.01) |
| C08G 61/12 | (2006.01) |
| C08K 5/3437 | (2006.01) |

(52) U.S. Cl.
CPC .............. *B01J 31/10* (2013.01); *B01J 31/0225* (2013.01); *C07D 215/06* (2013.01); *C08G 61/122* (2013.01); *C08K 5/3437* (2013.01); *B01J 2231/14* (2013.01); *B01J 2231/342* (2013.01); *C08G 2261/344* (2013.01); *C08G 2261/43* (2013.01)

(58) Field of Classification Search
CPC ............. B01J 31/0225; B01J 2231/342; B01J 2231/14; B01J 31/10; C08G 61/122; C08G 2261/43; C08G 2261/344; C07D 215/06
USPC ........................................................ 252/404
See application file for complete search history.

(56) References Cited

U.S. PATENT DOCUMENTS

| | | | |
|---|---|---|---|
| 4,326,062 A | 4/1982 | Kojima et al. | |
| 4,514,570 A | 4/1985 | Bowers, Jr. | |

FOREIGN PATENT DOCUMENTS

| | | |
|---|---|---|
| JP | 55-040661 A | 3/1980 |
| JP | 58-088363 A | 5/1983 |
| WO | WO 2005042154 A1 | 5/2005 |

OTHER PUBLICATIONS

Wang, Xiaoshu et al., Analysis of the Technology for Synthesizing antioxidant RD, Tire Industry, vol. 25(12), pp. 711-715 (2005), China.
Qian, Qinghua et al., Catalyst Sifting of Producing RD with Aniline and Acetone, Advances Sciences & Technology, vol. 17(8), pp. 21-24 (2003), China.
Diaion SK-104, Strongly Acidic Cation Exchange Resins pamphlet, see http://www.itochu-ca.com/docs/product/00500-013.pdf, date of publication is unknown.

*Primary Examiner* — Ling Choi
*Assistant Examiner* — Catherine S Branch
(74) *Attorney, Agent, or Firm* — Manni Li; Mei & Mark LLP

(57) ABSTRACT

A process for using a solid acid catalyst having a strong acid cation exchange resin having a cross-linking network structure and free aromatic sulfonic acids adsorbed in the network for synthesis of rubber antioxidant RD and other strong-acid catalyzed reactions.

20 Claims, 2 Drawing Sheets

SOLID ACID CATALYST AND METHOD FOR PREPARING AND USING THE SAME

CROSS-REFERENCE TO RELATED APPLICATIONS

The subject application is a divisional application of U.S. patent application Ser. No. 12/943,930 filed on Nov. 10, 2010, now allowed, which claims priority on Chinese Patent Application Nos. 200910215840.9 filed on Dec. 30, 2009 and 201010110589.2 filed on Feb. 12, 2010. The subject matters and contents of the above mentioned domestic and foreign priority applications are incorporated herein by reference.

FIELD OF THE INVENTION

The present invention relates to a catalyst, particularly, a solid acid catalyst.

DESCRIPTION OF THE RELATED ART

Rubber antidegradant RD is a ketoamine type rubber antioxidant in the powdery or sheet form with a light yellow or amber color. RD is a mixture of oligomers of 2,2,4-trimethyl-1,2-dihydroquinoline, including dimers, trimers, and tetramers. RD is one of the most popular rubber antioxidants in the global market.

RD is synthesized by an acid-catalyzed condensation reaction using aniline and acetone as the starting material under a temperature of 130-140° C. to form the monomers and polymerization of the monomers to obtain the oligomer mixture RD. Both one-step and two-step processes have been used for making RD. In the one-step process, the condensation reaction to form the monomers and the polymerization reaction of the monomers occur simultaneously in the same step, then, excess reactants are removed from the mixture to obtain the finished products; in the two-step process, the condensation reaction occurs first to form monomers, followed by the removal of excess reactants from the reaction mixture and the polymerization of the monomers under acidic condition to form the oligomer mixture. The two-step process is time consuming with higher energy consumption while achieving higher contents of oligomers in the product; the one-step process is simple with lower energy consumption but results in lower contents of the oligomers in the product.

Acid catalysts for making RD are classified into two categories: the protonic acid catalyst and the Lewis acid catalyst, and different catalysts are selected for use in the condensation and polymerization reactions, respectively, to achieve better results. See Analysis of the Technology for Synthesizing antioxidant RD, Wang, Xiaoshu et al., Tire Industry, Vol. 25(12), pages 711-715 (2005). The recovery of the protonic acid catalyst and Lewis acid catalyst is very difficult according to the article. For example, Japanese Patent No. JP58-088363 discloses the conventional method of preparing RD by using hydrochloric acid as a liquid catalyst, and in the post treatment step, sodium hydroxide is added to consume hydrochloric acid and the catalyst cannot be recovered. Additionally, hydrochloric acid, the conventional catalyst used in the synthesis of RD, has the disadvantages of low conversion rate of aniline, poor product quality, serious environmental pollution, stringent requirement for production facilities, and longer production period.

U.S. Pat. No. 4,514,570 discloses a process for preparing 2,2,4-trimethyl-1,2-dihydroquinoline compounds by reacting acetone with an aniline compound in the presence of a strong acidic sulfonic acid-type macroreticular cation exchange resin catalyst. However, the working conditions for the macroreticular cation exchange resin are not optimal: the temperature of the reaction is very high, the reaction time is as long as 48 hours while the reaction is conducted batchwise, and the starting materials are different from those for making RD as in the example. The energy consumption in the reaction is high, and it is not suitable for industrial application.

Qian, Qinghua et al., the Catalyst Sifting of Producing RD with Aniline and Acetone, Advances Sciences & Technology, Vol. 17(8), pages 21-24 (2003), discloses the catalysts for the reaction of aniline and acetone for making RD, and that strong acidic ion exchange resin had better conversion rate of aniline than other solid acids. However, the strong acid cation exchange resin has a low effective acid content, poor thermoresistance, and requires longer reaction time which is more than about 16 hours. Additionally, the catalyst is difficult to recover because of fragility, high consumption rate, and thus unsuitable for industrial production.

Japanese Patent No. JP 55-40661 discloses a process for preparing antioxidant RD by condensation reaction of aniline and acetone and using p-toluene sulfonic acid as the catalyst. Although the reactivity is high, amount of the catalyst used is high, leading to difficulties in the recovery of the catalyst. In addition, yield is low, the cost for production is high, the synthesis of the monomers is difficult to control, the components of the product are complicated, and the environment pollution is serious.

BRIEF SUMMARY OF THE INVENTION

The present invention provides a solid acid catalyst with high catalytic reactivity. The solid acid catalyst of the present invention has a strong acid cation exchange resin having a cross-linking network and free aromatic sulfonic acids adsorbed in the network. The strong acid cation exchange resin has been compounded with the aromatic sulfonic acids. Preferably, the strong acid cation exchange resin is based on styrene or acrylic acid (ester) or both and cross-linked by divinyl benzene, and contains sulfonic acid groups as the strong acid group.

The present invention further provides a process for preparing the solid acid catalyst by stirring a strong acid cation exchange resin and aromatic sulfonic acids in a hydrochloric acid solution to form a mixture, letting the mixture stand for a period of time, isolating solid material from the mixture, and drying the solid material to obtain the solid acid catalyst.

The present invention also provides a method for using the solid acid catalyst in a reaction for making the rubber antioxidant RD.

The present invention further provides a process for preparing rubber antioxidant RD that is easier to operate with high conversion rate. The rubber antioxidant RD is prepared by feeding aniline or its derivatives into a reaction tower from the top of the tower, feeding gasified acetone or its derivatives into the tower from the bottom of the tower, reacting the aniline or its derivatives and acetone or its derivatives to form a reaction mixture under suitable conditions in the tower, recovering excess acetone or its derivatives and water generated in the reaction mixture during the reaction through the top of the tower, and collecting the reaction mixture with a receiving device at the bottom of the tower. The tower contains reaction beds that are loaded with the solid acid catalysts of the present invention.

In the reaction tower, the condensation of aniline or derivative thereof and acetone or derivative thereof to generate 2,2,4-trimethyl-1,2-dihydroquinoline monomers and the polymerization of the monomers to yield the rubber antioxi-
} dant RD may take place simultaneously in the presence of the solid acid catalyst-loaded reaction beds. Alternatively, the condensation reaction of the aniline or derivative thereof and the acetone or derivative thereof to yield 2,2,4-trimethyl-1,2-dihydroquinoline monomers proceeds in the tower under atmospheric pressure without the polymerization reaction, and the monomers are distilled off from the reaction mixture and polymerized to dimers or other oligomers in high purity in a reaction vessel other than the reaction tower. The process of the present invention may be conducted as a batchwise or continuous process.

The composite solid acid catalyst of the present invention has significantly improved acid-catalyzing reactivity. When applied to the reaction for synthesizing the antioxidant RD, the composite solid acid catalyst improves the selectivity for the RD monomers, reduces the formation of the byproducts, and can be recycled to eliminate the generation of wastes.

DETAILED DESCRIPTION OF THE INVENTION

Figure 1:
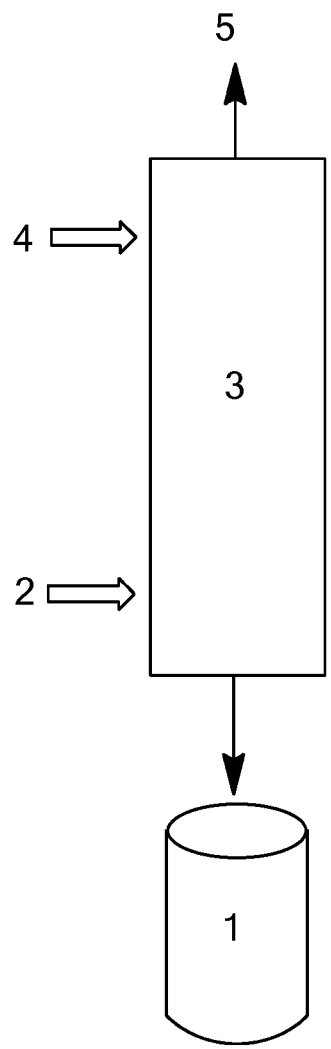
FIG. 1 illustrates the reaction equipment used in one example of the present invention.

The solid acid catalyst of the present invention comprises a strong acid cation exchange resin having a cross-linking network and free aromatic sulfonic acids adsorbed in the cross-linking network structure of the resin. The strong acid cation exchange resin has been compounded with the aromatic sulfonic acids. The free aromatic sulfonic acids comprise about 0.01 to 3% by weight of the total weight of the catalyst.

The solid acid catalyst of the present invention is produced by compounding a strong acid cation exchange resin with aromatic sulfonic acids. The strong acid cation exchange resin has a porous network structure. The aromatic sulfonic acids are of strong polarity and prone to being adsorbed by the porous network structure of the strong acid cation exchange resin, thus, the aromatic sulfonic acids are entrapped in the network and are not easily released from the network structure.

The matrix of the strong acid cation exchange resin used in the present invention may be a polymer of styrene or acrylic acid (ester) or both and typically having a stereo-network structure cross-linked by divinyl benzene. The matrix can also be made from other organic monomers, such as phenol formaldehydes (fp), epoxys (epa), vinyl pyridines (vp), urea-formaldehydes (ua) and the like. The strong acid group in the resin is typically a sulfonic acid group. However, other acid groups, such as —COOH, can also hang on the resin matrix. Preferably, the strong acid cation exchange resin includes, but is not limited to, 732 Cation Exchange Resin, 734 Cation Exchange Resin, DH Cation Exchange Resin, D001 Cation Exchange Resin, D002 Cation Exchange Resin, D061 Cation Exchange Resin, D072 Cation Exchange Resin, JK008 Cation Exchange Resin, or a mixture thereof. These strong acid cation exchange resin are known to one of ordinary skill in the art and commercially available on the market. More preferably, the strong acid cation exchange resin is a styrene-divinyl benzenes strong acid cation exchange resin. Most preferably, the strong acid cation exchange resin is D002 Cation Exchange Resin.

The aromatic sulfonic acids to be used in the present invention may be benzene sulfonic acid, a monoalkyl benzene sulfonic acids, a dialkyl benzene sulfonic acids, a multi-alkyl benzene sulfonic acid, a halo-benzene sulfonic acid, an optionally substituted benzene disulfonic acid with the substitution on the benzene ring, an optionally substituted trisulfonic acid with the substitution on the benzene ring, or a mixture thereof The aromatic sulfonic acid usually has one optionally substituted benzene ring which bearing one or two sulfonic groups. Examples of the aromatic sulfonic acids include, but not limited to, benzene sulfonic acid; monoalkyl benzene sulfonic acids, such as p-toluene sulfonic acid, o-toluene sulfonic acid, m-toluene sulfonic acid, and p-ethyl benzene sulfonic acid; dialkyl benzene sulfonic acids and multi-alkyl benzene sulfonic acids, such as dimethyl benzene sulfonic acids, for examples, 2,4-dimethyl benzene sulfonic acid, 3,4-dimethyl benzene sulfonic acid, 2,6-dimethyl benzene sulfonic acid, 2,3-dimethyl benzene sulfonic acid, and diethyl benzene sulfonic acids; dihalo- or multi-halo-benzene sulfonic acids, such as p-(o-, m-)fluoro-benzene sulfonic acid and p-(o-, m-)chloro-benzene sulfonic acid; corresponding disulfonic acids or multi-sulfonic acid, such as p-(o-, m-)benzene disulfonic acid; or the combination thereof. Among the aromatic sulfonic acids, p-(o-, m-)toluene sulfonic acid, p-fluoro-(chloro-)benzene sulfonic acid, p-(o-, m-)benzene disulfonic acid are preferred; p-(o-, m-)toluene sulfonic acid is more preferred; p-toluene sulfonic acid is the most preferred.

The amount of the aromatic sulfonic acids introduced into the ion exchange resin varies depending on specific applications of the catalyst. Typically, the weight of the aromatic sulfonic acid introduced varies from 0.001 to 0.5 times of the weight of the exchange resin, preferably, no more than 0.4 times, more preferably, no more than 0.3 times, and most preferably between 0.01 to 0.2 times. In one embodiment of the present invention, the composite solid acid catalyst is a composite of cation exchange resin D002 and p-toluene sulfonic acid. The weight ratio of D002 to p-toluene sulfonic acid is about 1:(0.001-0.5), preferably 1:(0.001-0.3), and more preferably 1:(0.01-0.2).

To prepare the catalyst of the present invention, the strong acid cation exchange resin is added to an aqueous solution of the aromatic sulfonic acid, and the mixture is stirred for a suitable period of time. Preferably, a suitable amount of hydrochloric acid may be added, and the concentration of hydrochloric acid in the aqueous solution is about 0.01-10% by weight, preferably about 0.1-7% by weight, and more preferably, about 1-5% by weight. The mixture may be stirred for about 30 minutes under atmospheric pressure at room temperature, and then let stand for 2 hours. The procedures are repeated for 1-2 times, then, the solid catalyst is separated by filtration and dried such as sun-dried or dried in the oven for 2 to 4 hours.

In some applications, the catalysts need to be reactivated after a long period of use. To reactivate the catalyst, the catalyst are stirred in a diluted hydrochloric acid solution for a suitable period of time.

The solid acid catalyst of the present invention is used for making rubber antioxidant RD. The solid acid catalyst may be useful in the condensation, polymerization, or both reactions, for making the rubber antioxidant. When using the solid acid catalyst of the present invention to synthesize the monomer of RD, 2,2,4-trimethyl-1,2-dihydroquinoline, the separation of the catalyst from the reaction mixture is easy, because the catalyst is insoluble in the reaction mixture. It eliminates complicated recovery process and discharge of pollutants. At the same time, the catalyst has a higher catalytic activity and long life-time.

The catalyst of the present invention can be used to catalyze reactions in a batchwise reaction pot or in a continuous tower (also referred to as the fixed bed or a trickle bed reaction). The continuous tower reaction is preferred, because the catalyst can be thoroughly immersed in the gas-liquid reaction phase, and the compounded aromatic sulfonic acid on the catalyst will not be released from the matrix, which greatly extends the life-span of the catalyst, while saving time in the time-consuming operations of catalyst separation, recovery, metering for the recycling, and continuous production is achieved with high production capacity and lower energy consumption and cost.

In the process for preparing rubber antioxidant RD, the rubber antioxidant is prepared by feeding aniline or a derivative thereof into a tower from the top of the tower, feeding gasified acetone or a derivative thereof into the tower from the bottom of the tower, reacting the aniline or derivative thereof and the acetone or derivative thereof in the reaction beds to form a reaction mixture under suitable conditions in the tower, distilling and recovering excess acetone or derivative thereof and water generated in the reaction from the top of the tower, and accumulating and collecting the liquid reaction mixture with a receiving device at the bottom of the tower. The tower contains reaction beds that are loaded with the solid acid catalyst of the present invention.

The process of the present invention is not limited to aniline and acetone as the starting materials and it is suitable to use aniline derivatives and/or acetone derivative as well. For examples, the acetone derivatives can be diacetone alcohol and mesityl oxide. When the raw materials rather than acetone and aniline are used, reaction conditions of the condensation or polymerization reactions, such as temperature, reaction time and the like, may be modified accordingly. These modifications are within the scope of the present invention.

The process of the present invention may be conducted in a batchwise process or continuous process.

In the batch process, aniline and the catalyst are added to a reaction kettle all at once, and acetone is added dropwise continuously. The weight ratio of aniline to the solid acid catalyst is about 1:(0.01-0.5), preferably 1:(0.01-0.25), and more preferably, 1: (0.15-0.2). If the amount of catalyst is too small, the catalytic activity is deficient and the conversion per pass of aniline is too low, leading to minimum industrial value; if the amount of catalyst is too large, the catalyst may be wasted and it also causes inconvenience to the operations of the batchwise production.

In the batch process, the feed amount of aniline to acetone is typically at a weight ratio of about 1:(1.25-10), preferably about 1:(3-7), and more preferably about 1:(5-7). If the amount of acetone is too small, water generated during the reaction can not be removed timely, which will lower the yield and increase side reactions. If the amount of acetone is too large, it will increase the cost for recovering acetone and waste the materials. The time for feeding and reaction is about 4-12 hours, preferably about 4-6 hours, under normal pressure and reaction temperature of about 80-150° C., preferably 120-140° C., and most preferably 130-135° C. Acetone and water generated during the reaction are distilled off the reaction and are directly separated and recovered by a distillation column. Recovered acetone is conveyed back to the raw material storage tank.

In the continuous tower reaction (also referred to as the fixed bed or a trickle bed reaction), the composite solid acid catalyst is one-time loaded on the reaction bed, aniline is continuously fed from the top of the tower, gasified acetone is fed from the bottom gas phase of the tower, and the reaction continuously proceeds in the tower.

FIG. 1 is a schematic view of the reaction vessel used in one example of the continuous tower reaction. As shown in FIG. 1, the reaction vessel includes a receiving tank for liquid reactants 1, an inlet for feeding gasified acetone 2, a reaction tower loaded with catalyst 3, an inlet for feeding aniline 4, and an outlet for discharging post-reaction acetone and water vapor 5.

The continuous tower process of the present invention may be a one-step process or a two-step process. In the one-step process, condensation and polymerization reactions proceed simultaneously under controlled conditions, and the reaction mixture may be directly distilled to obtain the product without specific treatment. In the two-step process, the reaction mixture after the condensation reaction is treated to obtain monomers of higher purity, and then, the monomers are polymerized.

In the embodiment of the present invention where the one-step process is used, the condensation of aniline or derivative thereof and acetone or derivative thereof to generate 2,2,4-trimethyl-1,2-dihydroquinoline monomers and polymerization of the 2,2,4-trimethyl-1,2-dihydroquinoline monomers to yield rubber antioxidant RD may take place simultaneously in the presence of the solid acid catalyst-loaded reaction beds in the tower. In the one-step process, the composite solid acid catalyst is loaded on the fixed beds in the tower. Aniline is continuously fed from the top of the tower, and gasified acetone is continuously fed from the bottom of tower. These materials continuously react in the tower under normal pressure and a temperature of 80-150° C., preferably 100-135° C., and more preferably 120-130° C. In order to achieve sufficient condensation and polymerization, the residence time of the materials in the tower is controlled, typically between 8-25 hours, preferably between 15-20 hours, and more preferably between 16-18 hours. On the other hand, the amount of acetone that is fed into the tower may be controlled with the weight ratio of aniline to acetone at about 1:(2-5), preferably 1:(2-3), and more preferably 1:(2-2.5). Excess acetone and water generated during the reaction are recovered by a distilling column connected to the top of the tower.

Further, the reaction mixture after the polymerization and containing RD flows into the receiving tank under the tower, and is distilled under reduced pressure, such as vacuum condition (e.g., −0.098 MPa), and at a temperature of about 220-250° C., preferably about 220-230° C., to recover the unreacted aniline and monomer. Antioxidant RD can be obtained by cooling the remaining reaction mixture and palletizing. The finished RD product contains about 25-35 wt % of dimers and 50-60 wt % of trimers and tetramers.

In another embodiment of the present invention where the two-step process is used, only the condensation reaction of the aniline or derivative thereof and the acetone or derivative thereof proceeds in the tower to yield 2,2,4-trimethyl-1,2-dihydroquinoline monomers under atmospheric pressure. Then, 2,2,4-trimethyl-1,2-dihydroquinoline monomers are distilled off from the condensation reaction mixture, and the monomers in high purity are polymerized to dimers or multimers in another reaction vessel.

Figure 2:
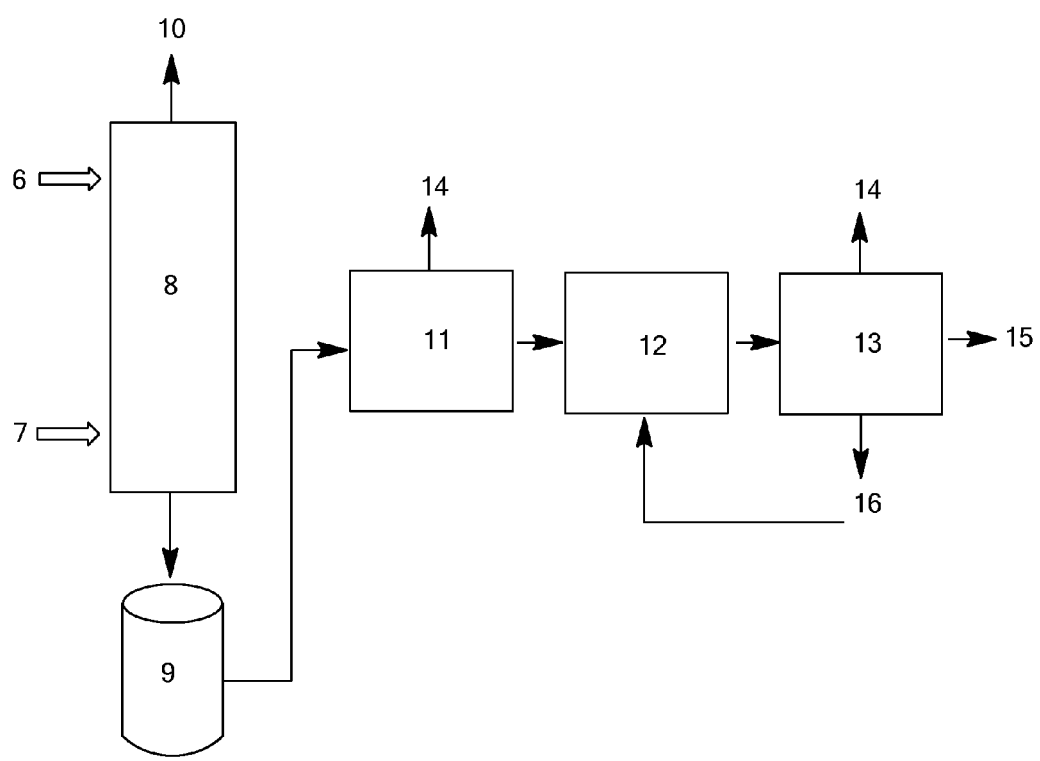
FIG. 2 is a flow chart depicting one embodiment of the process for preparing rubber antioxidant of the present invention.

In the two-step process, the resultant liquid mixture after the condensation reaction directly goes into polymerization. FIG. 2 is a flow chart illustrating the embodiment. In particular, aniline 6 and gasified acetone 7 are fed into the reaction tower with catalytic beds 8 under normal pressure. The weight ratio of aniline to acetone is about 1:(2-10), preferably about 1:(3-7), and more preferably 1:(5-7). The residence time in the tower is about 0.5-10 hours, preferably 1-8 hours, and more preferably 2-6 hours. The temperature of the reaction beds in the tower is at about 80-150° C., preferably about 100-135° C., and more preferably 120-130° C. Aniline and acetone continuously react in the reaction beds loaded with the solid acid catalysts of the present invention. The excess acetone and water generated in the condensation are recovered continuously by means of a distilling column connected to the tower top 10. The condensation liquid containing monomers of antioxidant RD, aniline, and a small amount of RD dimers and trimers continuously flows into the receiving tank 9. After the removal of excess aniline 14 under the reduced pressure in an aniline distillation kettle 11, the mixture is conveyed into a polymerization kettle 12, and after adjusting acidity, the mixture is polymerized under normal pressure and at a temperature of about 70-130° C., preferably 80-110° C., and more preferably 95-105° C., for 4-10 hours, preferably 4-8 hours, and more preferably 4-6 hours.

Further, the reaction mixture is conveyed to the distillation kettle 13 as shown in FIG. 2 for the post-treatment. In the post-treatment step, acidic substances, e.g., hydrochloric acid, and unreacted aniline 14 are removed from the mixture. In order to remove the acidic substances, suitable amount of alkali solution may be added to neutralize the acid. Preferably, an organic solvent is introduced so as to reduce the amount of the monomers or polymers dissolved in the aqueous solution. In one embodiment, the mixture is diluted with toluene and then neutralized by a diluted alkali solution (KOH, NaOH, and the like). Then, the aqueous layer is removed, and the oil layer is kept under normal pressure to recover toluene, followed by distillation under −0.098 MPa and at about 220-250° C., preferably 220-230° C., to recover unreacted monomers 16. Finished products of antioxidant RD (15) are obtained by cooling the residue and palletizing. The finished product contains about 50-60 wt % of dimers and a total of 70-80 wt % oligomers including the dimers, trimers, and tetramers. As shown in FIG. 2, recovered monomers 11 may be conveyed to the polymerization kettle 7 for the polymerization reaction.

In another embodiment of the two-step process, the monomers produced in the condensation reaction are distilled off from the reaction mixture, then the distilled monomers with high purity are polymerized to produce dimers and polymers. Specifically, the liquid mixture flowing into the receiving tank under the tower is distilled under reduced pressure to recover unreacted aniline, then to recover 2,2,4-trimethyl-1,2-dihydroquinoline monomers, with the monomer content being controlled to be ≥85%, preferably ≥90%, and more preferably ≥94%. Hydrochloric acid are added to the distilled monomers to adjust the pH value, then, the monomers are polymerized under normal pressure. The embodiment achieves higher product quality in that the content of dimers is typically about 60-70% and the content of oligomers (dimers, trimers and tetramers) is about 80-90% in total.

Therefore, in the processes of the present invention, the two-step process is preferred as it achieves higher content of the dimer, and the total content of the oligomers is also higher than that of the one-step process.

When antioxidant RD is prepared by using the composite solid acid catalyst of the present invention, the conversion rate of the condensation reaction based on aniline reaches more than 75%, the purity of the monomer is up to 75%-94%, the content of the dimer is up to 50-70%, and the total content of dimers, trimers, and tetramers is up to 70-85% in total.

Compared to the existing process for the synthesis, the catalyst of the present invention has the advantages of simple process, mild reaction conditions, higher product yield, higher contents of dimers in the finished products RD. The products have superior antioxidant quality. The process does not discharges waste materials and requires lower production cost. The process may be conducted continuously and meet the requirements of green chemistry. The process is very suitable for industrial application.

The present invention is further illustrated in the following examples, however, the examples and figures do not serve to limit the scope of the present invention. Various modifications and variations can be made based on the description of the present invention without departing from the scope of the present invention.

Example 1

Strong acid cation exchange resin D002 100 g was added to a 500 ml three-neck flask equipped with a stirrer, a thermometer, and an exhaustion system used to condense and absorb the tail gas. Then, 7.5 g p-toluene sulfonic acid was added to the flask, followed by 250 g 5% hydrochloric acid solution. The mixture was stirred for 30 minutes under room temperature and the atmosphere pressure, and let stand for 2 hours. After repeating 1-2 times of the previous procedures, the solid catalyst was separated by filtration, sun-dried and dried in an oven for 2-4 hours. The catalyst was cooled down and ready for use.

Example 2

Batchwise Process

Aniline 250 g and 50 g catalyst of Example 1 were fed into a 1000 ml four-neck flask equipped with a stirrer, a thermometer, and a discharging tube (connected to a distillation column and used to guide acetone and water generated in the reaction to enter the column). Acetone 1750 g acetone was continuously fed into the mixture by a metering pump, and the feed and reaction time lasted 8 hours, under normal pressure and 135-140° C. Water generated during the reaction and excess acetone were recovered by a distillation column. The conversion per pass of aniline in the condensation reaction was 78%.

Aniline was removed from the condensation liquid under vacuum condition of −0.098 MPa, and 17.5 g (30%) hydrochloric acid was added to adjust the pH. Then, the material was polymerized for 6 hours under normal pressure and 95-100° C. Next, the mixture was diluted with 50 g toluene, neutralized with 30% alkali solution (NaOH), allowed to stand still to separate layers, and the aqueous layer was removed while toluene was recovered from the oil layer under normal pressure. The residual monomers were recovered under −0.098 MPa and 220-230° C. for recycling and reuse.

The polymerization conversion rate per pass of the monomers was 70%, the residue was cooled and palletized to produce 135 g antioxidant RD end product, giving yield per pass of 54%, and a total yield of 98% when the recycled aniline and monomers were counted. The end product contained 52% of dimer and 74% of oligomers in total (including dimer, trimer, and tetramer).

Example 3

Two-Step Process in Continuous Tower Reaction

The solid acid catalyst prepared in Example 1 was used in a continuous tower reaction. Catalyst 50 g was loaded into a tower, aniline and acetone were continuously fed into the tower at a weight ratio of 1:(5-7), with aniline entering from the top of the tower and gasified acetone from the bottom of the tower. The tower was kept under normal pressure and a temperature of 120-130° C., the residence time of raw materials was 4 hours. The water generated during the reaction and excess acetone were recovered by a distillation column connected to the top of the tower and then separated from one another. The resulting liquid mixture continuously flew into the receiving tank under the tower. The flow chart of the example was shown in FIG. 2. The conversion rate of aniline was 82%. Aniline was removed from 175 g condensation liquid via vacuum distillation under −0.098 MPa, 17.5 g (30%) hydrochloric acid was added to adjust acidity, and the mixture underwent polymerization for 6 hours under normal pressure and 95-100° C.

Next, the mixture was diluted with 50 g toluene, neutralized with 30% alkali solution (NaOH), allowed to stand still to separate layers, and the aqueous layer was removed. Toluene was recovered from the oil layer under normal pressure, and residual monomers recovered under −0.098 MPa and 220-230° C. for recycling.

The conversion rate per pass of the monomer in the polymerization reaction was 73%. The residue was cooled and palletized to produce 140 g antioxidant RD as the end product, giving a yield per pass of 61%, and a total yield of 99% when the recycled aniline and monomer were counted. The end product contained 54% of dimers and 76% of oligomers in total (including dimer, trimer and tetramer).

Compared with the batchwise process in Example 2, the continuous reaction process in Example 3 got a slightly higher conversion per pass of aniline and a higher content of dimers in the end products. In addition, Example 3 skipped filtration and recycling of the catalyst, thus reducing cost for material and environment pollution in these steps, and is more suitable for industrial application.

Comparative Example 1

In Batch Mode

Aniline 250 g and resin D002 50 g were added in a 1000 ml four-neck flask equipped with a stirrer, a thermometer, and a discharging tube (connected to a distillation column and used to guide acetone and water generated in the reaction into the column). Acetone 1750 g was continuously fed by a metering pump into the mixture and the feed and reaction time lasted 8 hours under normal pressure and at 135-140° C. Water generated during the reaction and excess acetone were recovered by the distillation column and then separated from each other. The conversion rate per pass of aniline in the condensation reaction was 32%. Aniline was removed from the condensation liquid via vacuum distillation under −0.098 MPa, 8 g (30%) hydrochloric acid was added to adjust acidity, and the mixture was polymerized for 6 hours under normal pressure and 95-100° C.

Next, the mixture was diluted with 50 g toluene, neutralized with 30% alkali solution (NaOH), allowed to stand still to separate layers, and the aqueous layer was removed. Toluene was recovered from the oil layer under normal pressure, and residual monomers were recovered under −0.098 MPa and 220-230° C. for recycling. The conversion rate per pass of the monomers in the polymerization was 68%, the residue was cooled and palletized to produce 50 g antioxidant RD end product, giving a yield per pass of 20%. The end product contained 50% of dimers and 72% of oligomers in total (including dimer, trimer and tetramer).

The results of Example 2 and Comparative Example 1 showed that, the conversion rate per pass of aniline in the condensation reaction was raised by about 1.5 times due to the use of the solid acid catalyst of the present invention.

Example 4

Two-Step Continuous-Tower Process

The solid acid catalyst prepared in Example 1 was used, but the reaction was in continuous-tower process. Composite solid acid catalyst 50 g was loaded into the tower, aniline and acetone were continuously fed into the tower at a weight ratio of 1:(3-4), with aniline entering from the top of the tower and gasified acetone from the bottom of the tower. The tower was kept under normal pressure and a temperature of 120-130° C., the residence time of raw materials was 4 hours. Water generated during the reaction and excess acetone were recovered by the distillation column connected to the top of the tower and then separated from each other. The resultant liquid mixture continuously flew into the receiving tank. The flow chart of the example was shown in FIG. 2. The conversion rate of aniline was 74%. Aniline was removed from the condensation liquid 175 g by vacuum distillation under −0.098 MPa, 14 g 30% hydrochloric acid was added to adjust acidity, and the mixture was polymerized for 6 hours under normal pressure and 95-100° C.

Next, the mixture was diluted with 50 g toluene, neutralized with 30% alkali solution (NaOH), allowed to stand still to separate layers, and the aqueous layer was removed. Toluene was recovered from the oil layer under normal pressure, and residual monomers were recovered under −0.098 MPa and at 220-230° C. for recycling. The conversion rate per pass of the monomers in the polymerization was 70%, the residue was cooled and palletized to produce 120 g antioxidant RD end product, giving a yield per pass of 52% and a total yield of 99% when the recycled aniline and monomer were counted. The end product contained 53% of dimers and 75% of oligomers in total (including dimer, trimer, and tetramer).

Comparing the results of Example 3 with Example 4, it showed that higher conversion rate per pass of aniline and higher yield per pass of the end product were achieved by introducing higher proportion of acetone.

Example 5

Two-Step Continuous-Tower Process

Condensation reaction was repeated as in Example 3. Aniline was removed from the condensation liquid 175 g by vacuum distillation under −0.098 MPa, and distillation was continued at 240-250° C. to collect 120 g monomers with a content of 85%. 30% hydrochloric acid 12 g was added to the monomers, and the monomers were polymerized for 6 hours under normal pressure and 95-100° C.

Next, the mixture was diluted with 50 g toluene, neutralized with 30% alkali solution (NaOH), allowed to stand still to separate layers, and the aqueous layer was removed. Toluene was recovered from the oil layer under normal pressure, and residual monomers were recovered under −0.098 MPa and 220-230° C. for recycling. The conversion rate per pass of the monomers in the polymerization reaction was 70%, the residue was cooled and palletized to produce 89 g end product, giving a yield per pass of 40%, and a total yield of 97% when the recycled aniline and monomer was counted. The end product contained 60% of dimers and 80% of oligomers in total (including dimer, trimer, and tetramer).

Example 6

One-Step Continuous-Tower Process

The solid acid catalyst prepared in Example 1 was used, in a continuous-tower reaction. Composite solid acid catalyst 50 g was loaded into the tower, aniline and acetone were continuously fed into the tower at a weight ratio of 1:1.5, with aniline entering from the top of the tower and gasified acetone from the bottom of the tower. The tower was maintained under normal pressure and a temperature of 120-130° C., the residence time of raw materials was 16-18 hours. Water generated during the reaction and excess acetone were recovered by the distillation column connected to the top of the reaction tower and then separated from each other. The resultant liquid mixture continuously flew into the receiving tank. The conversion rate of aniline was 80%.

Aniline was removed from the resultant liquid mixture by vacuum distillation under −0.098 MPa and at 220° C. The residue was cooled and palletized to produce antioxidant RD end product. The end product contained 35% of dimers and 56% of oligomers in total (including dimer, trimer, and tetramer).

Example 6 showed that the one-step process using fixed beds did not make a notable difference from the two-step process as for conversion rate per pass of the condensation of acetone and aniline, it nevertheless got a lower content of the dimers in the end product, of which a larger part were trimers and tetramers. One possible reason was that the amount of acetone used in the one-step method was lower, so water generated in the reaction was not sufficiently brought out by the distilled acetone, thus limiting the condensation reaction.

Comparative Example 2

The solid acid catalyst of the present invention was prepared according to Example 1, except that the same amount of strong acid cation exchange resin 732 was used instead of resin D002, giving the catalyst of Control 1.

The steps in Example 2 were repeated, using Control 1 instead of the catalyst in Example 2. The results were: the conversion per pass of aniline in the condensation reaction was 39%, the conversion rate per pass of the monomers in the polymerization reaction was 70%. Antioxidant RD 67.5 g was obtained with a yield per pass at 27%, and a total yield (effective yield) of 98% when the recycled aniline and monomers was counted. The end product contained 52% of dimers and 74% of oligomers in total (including dimer, trimer, and tetramer).

Comparative Example 3

The solid acid catalyst of the present invention was prepared according to Example 1, except that the same amount of strong acid cation exchange resin JK008 was used instead of resin D002, giving the catalyst of Control 2.

The steps in Example 2 were repeated, using Control 2 instead of the catalyst of Example 2. The results were: the conversion per pass of aniline in the condensation reaction was 30%, the conversion per pass of the monomers in the polymerization reaction was 70%, 51.9 g antioxidant RD was obtained with a yield per pass at 20.8% and a total yield (effective yield) of 97% when the recycled aniline and monomers were counted. The end product contained 50% of dimers and 70% of oligomers in total (including dimer, trimer, and tetramer).

I claim:

1. A process for preparing rubber antioxidant RD, comprising
    feeding aniline or a derivative thereof into a tower from a top of the tower,
    feeding gasified acetone or a derivative thereof into the tower from a bottom of the tower,
    reacting the aniline or the derivative thereof and the acetone or the derivative thereof to form a reaction mixture comprising 2,2,4-trimethyl-1,2-dihydroquinoline monomers in presence of a solid acid catalyst under suitable conditions in the tower,
    polymerizing the reaction mixture comprising 2,2,4-trimethyl-1,2-dihydroquinoline monomers to form a rubber antioxidant RD, and
    recovering excess acetone or derivative thereof and water generated during the reaction by a distillation column connected to the tower,
    wherein the solid acid catalyst is loaded on reaction beds in the tower, and the solid acid catalyst comprises a strong acid cation exchange resin having a cross-linking network and free aromatic sulfonic acids adsorbed in the cross-linking network structure.

2. The process according to claim 1, wherein condensation of the aniline or derivative thereof and the acetone or the derivative thereof to generate 2,2,4-trimethyl-1,2-dihydroquinoline monomers and polymerization of the 2,2,4-trimethyl-1,2-dihydroquinoline monomers to yield the rubber antioxidant RD takes place simultaneously in the tower in presence of the solid acid catalyst-loaded reaction beds.

3. The process according to claim 1, wherein the reaction beds are kept at about 100-135° C. during the reactions, and residence time of the aniline or derivative thereof and the acetone or derivative thereof in the tower is about 15-20 hours.

4. The process according to claim 1, further comprising
    recovering unreacted aniline and the 2,2,4-trimethyl-1,2-dihydroquinoline monomers from the reaction mixture under reduced pressure and at a temperature of about 220-230° C.

5. The process according to claim 1, wherein condensation reaction of the aniline or the derivative thereof and the acetone or the derivative thereof to yield the 2,2,4-trimethyl-1,2-dihydroquinoline monomers proceeds in the tower under atmospheric pressure, the reaction bed are kept at about 100-135° C. during the condensation reaction, and residence time of the aniline or derivative thereof and the acetone or derivative thereof in the tower is about 2-7 hours, and polymerization of the 2,2,4-trimethyl-1,2-dihydroquinoline monomers occurs outside the tower.

6. The process according to claim 5, wherein a feed ratio of the aniline or derivative thereof to the acetone or derivative thereof is about 1:(5-7) by weight.

7. The process according to claim 5, further comprising
    recovering unreacted aniline and monomers from the reaction mixture under reduced pressure at about 220-230° C.

8. The process according to claim 5, further comprising
    distilling out the 2,2,4-trimethyl-1,2-dihydroquinoline monomers from the reaction mixture, and
    polymerizing the 2,2,4-trimethyl-1,2-dihydroquinoline monomers to dimers or multimers in high purity in a separate reaction vessel.

9. The process according to claim 1, wherein the strong acid cation exchange resin is based on styrene, acrylic acid (ester), or both, and cross-linked by divinyl benzene, and bears sulfonic groups.

10. The process according to claim 1, wherein the aromatic sulfonic acid is selected from the group consisting of benzene sulfonic acid, p-toluene sulfonic acid, o-toluene sulfonic acid, m-toluene sulfonic acid, p-ethyl benzene sulfonic acid, dimethyl benzene sulfonic acid, p-fluoro-benzene sulfonic acid, o-fluoro-benzene sulfonic acid, m-fluoro-benzene sulfonic acid, p-chloro-benzene sulfonic acid, o-chloro-benzene sulfonic acid, m-chloro-benzene sulfonic acid, p-benzene disulfonic acid, o-benzene disulfonic acid, m-benzene disulfonic acid, and a mixture thereof.

11. The process according to claim 1, wherein the process is conducted as a continuous process and each step is conducted continuously.

12. The process according to claim 1, wherein the strong acid cation exchange resin is based on styrene, is cross-linked by divinyl benzene, and bears sulfonic groups.

13. The process according to claim 1, wherein the strong acid cation exchange resin is selected from the group consisting of Cation Exchange Resin 732, Cation Exchange Resin 734, Cation Exchange Resin DH, Cation Exchange Resin D001, Cation Exchange Resin D002, Cation Exchange Resin D061, Cation Exchange Resin D072, Cation Exchange Resin JK008, and a mixture thereof.

14. The process according to claim 1, wherein the free aromatic sulfonic acids are about 0.01 to 3% by weight of total weight of the catalyst.

15. The process according to claim 1, wherein the aromatic sulfonic acids are selected from the group consisting of benzene sulfonic acid, a monoalkyl benzene sulfonic acids, a dialkyl benzene sulfonic acids, a multi-alkyl benzene sulfonic acid, a halo-benzene sulfonic acid, an optionally substituted benzene disulfonic acid, an optionally substituted trisulfonic acid, and a mixture thereof.

16. The process according to claim 1, wherein the aromatic sulfonic acid is selected from the group consisting of benzene sulfonic acid, p-toluene sulfonic acid, o-toluene sulfonic acid, m-toluene sulfonic acid, p-ethyl benzene sulfonic acid, dimethyl benzene sulfonic acid, p-fluoro-benzene sulfonic acid, o-fluoro-benzene sulfonic acid, m-fluoro-benzene sulfonic acid, p-chloro-benzene sulfonic acid, o-chloro-benzene sulfonic acid, m-chloro-benzene sulfonic acid, p-benzene disulfonic acid, o-benzene disulfonic acid, m-benzene disulfonic acid, and a mixture thereof.

17. The process according to claim 1, wherein the solid acid catalyst is a compound of Cation Exchange Resin D002 and p-toluene sulfonic acid.

18. The process according to claim 17, wherein weight ratio of Cation Exchange Resin D002 to p-toluene sulfonic acid is about 1:(0.001-0.5).

19. The process according to claim 18, wherein weight ratio of Cation Exchange Resin D002 to p-toluene sulfonic acid is about 1:(0.01-0.2).

20. A method for using a solid acid catalyst according to claim 1, comprising
applying the solid acid catalyst as described in claim 1 in the reaction for making rubber antioxidant RD.

* * * * *